United States Patent
Takada

(10) Patent No.: US 6,936,824 B2
(45) Date of Patent: Aug. 30, 2005

(54) PORTABLE APPARATUS AND METHOD FOR MONITORING USER'S SKIN

(75) Inventor: Eri Takada, Tokyo (JP)

(73) Assignee: Konami Corporation, Tokyo (JP)

( * ) Notice: Subject to any disclaimer, the term of this patent is extended or adjusted under 35 U.S.C. 154(b) by 29 days.

(21) Appl. No.: 10/059,865

(22) Filed: Jan. 30, 2002

(65) Prior Publication Data

US 2002/0115926 A1 Aug. 22, 2002

(30) Foreign Application Priority Data

Feb. 1, 2001 (JP) .......................................... 2001-026131

(51) Int. Cl.$^7$ ................................................ G01J 5/32
(52) U.S. Cl. ...................................... 250/372; 702/176
(58) Field of Search ....................... 250/372; 600/407; 702/176; 377/20

(56) References Cited

U.S. PATENT DOCUMENTS

| | | | |
|---|---|---|---|
| 3,903,423 A | | 9/1975 | Zweig ...................... 250/474.1 |
| 4,428,050 A | | 1/1984 | Pellegrino et al. .......... 250/372 |
| 4,535,244 A | * | 8/1985 | Burnham .................... 250/372 |
| 4,985,632 A | * | 1/1991 | Bianco et al. ............... 250/372 |
| 5,008,548 A | * | 4/1991 | Gat .......................... 250/372 |
| 5,036,311 A | * | 7/1991 | Moran et al. ................ 340/600 |
| 5,306,917 A | * | 4/1994 | Black et al. ................ 250/372 |
| 6,321,177 B1 | * | 11/2001 | Ferrero et al. .............. 702/166 |
| 6,484,932 B1 | * | 11/2002 | Kinney et al. ................ 235/73 |
| 2003/0065255 A1 | * | 4/2003 | Giacchetti et al. .......... 600/407 |

FOREIGN PATENT DOCUMENTS

| | | |
|---|---|---|
| CN | 2075788 | 4/2004 |
| DE | 40 12 984 | 4/1990 |
| FR | 2 658 410 | 9/1985 |
| FR | 2 587 117 | 2/1990 |
| GB | 2 181 833 | 4/1987 |
| JP | 6-4289 | 2/1994 |
| JP | 265138 | 6/1997 |
| JP | 2000-175871 | 6/2000 |

* cited by examiner

Primary Examiner—R. Alexander Smith
(74) Attorney, Agent, or Firm—Bachman & LaPointe, P.C.

(57) ABSTRACT

This portable apparatus comprises a housing having a circuit built-in, and an input key, an ultraviolet receptive opening and a display, which are combined with the housing as one body. An ultraviolet sensor is provided in the interior of the ultraviolet receptive opening. This portable apparatus comprises means for receiving characteristic data about a characteristic of a user's skin against a suntan from the input key and measurement data about an ultraviolet ray quantity from the ultraviolet sensor, for predicting a user's suntanned skin condition from these data, and for generating image data for displaying an image about the prediction of user's suntanned skin condition. The image, which is based on image data generated by this means, is displayed on the display, making it possible for the user to confirm the user's skin condition.

20 Claims, 12 Drawing Sheets

FIG. 6

FIRST BASIC DATA

| PREDICTION / SKIN LEVEL | 1 | 2 | 3 | 4 | 5 |
|---|---|---|---|---|---|
| A) SAFE | ~10kJ/m² | ~13.3kJ/m² | ~16.6kJ/m² | ~20kJ/m² | ~23.3kJ/m² |
| B) RATHER SAFE | ~20kJ/m² | ~26.6kJ/m² | ~33.3kJ/m² | ~40kJ/m² | ~46.6kJ/m² |
| C) SLIGHTLY DANGEROUS | ~30kJ/m² | ~40kJ/m² | ~50kJ/m² | ~60kJ/m² | ~70kJ/m² |
| D) RATHER DANGEROUS | ~40kJ/m² | ~50kJ/m² | ~60kJ/m² | ~70kJ/m² | ~80kJ/m² |
| E) DANGEROUS | ~50kJ/m² | ~60kJ/m² | ~70kJ/m² | ~80kJ/m² | ~90kJ/m² |

SECOND BASIC DATA

| PREDICTION / SKIN LEVEL | 1 | 2 | 3 | 4 | 5 |
|---|---|---|---|---|---|
| A) SAFE | ~13.3kJ/m² | ~16.6kJ/m² | ~20kJ/m² | ~23.3kJ/m² | ~26.6kJ/m² |
| B) RATHER SAFE | ~26.6kJ/m² | ~33.3kJ/m² | ~40kJ/m² | ~46.6kJ/m² | ~53.3kJ/m² |
| C) SLIGHTLY DANGEROUS | ~40kJ/m² | ~50kJ/m² | ~60kJ/m² | ~70kJ/m² | ~80kJ/m² |
| D) RATHER DANGEROUS | ~50kJ/m² | ~60kJ/m² | ~70kJ/m² | ~80kJ/m² | ~90kJ/m² |
| E) DANGEROUS | ~60kJ/m² | ~70kJ/m² | ~80kJ/m² | ~90kJ/m² | ~100kJ/m² |

FIG. 7A

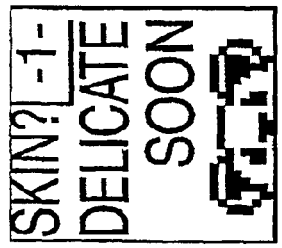

FIG. 7B

| SKIN LEVEL NUMERAL VALUE DISPLAYING SECTION | SKIN LEVEL DISPLAYING SECTION | EXPLANATION DISPLAYING SECTION |
|---|---|---|
| 1 | DELICATE | THE SKIN BECOMES RED-HOT SOON AND NO SUNTANNED |
| 2 | RATHER DELICATE | THE SKIN BECOMES RED-HOT EASILY AND NO SUNTANNED EASILY |
| 3 | NORMAL | THE SKIN BECOMES RED-HOT FIRST, BUT SUNTANNED GRADUALLY |
| 4 | RATHER STRONG | THE SKIN BECOMES LITTLE RED-HOT AND SUNTANNED WELL |
| 5 | STRONG | THE SKIN DOES NOT BECOME RED-HOT AND SUNTANNED EASILY |

FIG. 10

| CUMULATIVE QUANTITY / CHARACTER LEVEL | 0 | | 1·2·3 | | 4·5 | | 6 | |
|---|---|---|---|---|---|---|---|---|
| A) SAFE | NAPPING IMAGE | (GOODBYE, I WILL GO OUT FOR A WHILE) (I'M NAPPING SINCE I FEEL SORE) | NAPPING IMAGE | (ZZZ..MOGU-MOGU SAFE, SAFE) (THE SKIN IS MORE DELICATE THAN YOU THINK...) | HAPPY IMAGE | (UV CARE IS THE PRIMARY KEY TO BEAUTY) (HUH!! KEEP ON GOING THIS WAY) | LOVE IMAGE | (YOU BECOME REALLY BEAUTIFUL, THESE DAYS?) (LA LA LA! KEEP ON GOING THIS WAY) |
| B) RATHER SAFE | GIVING-UP IMAGE | (TAKE CARE OF YOUR SKIN) | GIVING-UP IMAGE | (I GUESS I WORK TOO HARD, I WANT TO TAKE A REST.) | NORMAL IMAGE | (MMM, WHAT A FEELING!) | SMILE IMAGE | (SKIN EXPOSED TO UV IS APT TO REDUCE ITS MOISTURE) |
| C) SLIGHTLY DANGEROUS | PRESSING IMAGE | IT'S USELESS TO SAY ANYTHING? I CANNOT MEET YOU AGAIN IF THE THING IS UNCHANGED. | PRESSING IMAGE | DON'T DO THAT. BE MORE CAREFUL. | PRESSING IMAGE | YOUR SKIN MAY BE DANGEROUS! | DISSATISFIED IMAGE | YOUR SKIN IS GETTING DANGEROUS UNLESS YOU TAKE CARE OF IT. |
| D) RATHER DANGEROUS | WARNING IMAGE | IT'S USELESS TO SAY ANYTHING? I CANNOT MEET YOU AGAIN IF THE THING IS UNCHANGED. | WARNING IMAGE | ARE YOU REALLY ALL RIGHT? YOU SHOULD GIVE A LOT OF CARE TO YOUR SKIN. | IRRITATING IMAGE | DON'T YOU HAVE A BEAUTIFUL SKIN? IT'S NO GOOD IF YOU KEEP GOING THIS WAY. | PRESSING IMAGE | OH, NO! I WANT TO GO TO THE PLACE OUT OF THE SUN. I HATE THIS PLACE. |
| E) DANGEROUS | DISAPPOINTING IMAGE | WE ARE FINISHED. GOODBYE. | DISAPPOINTING IMAGE | OH, I'M AMAZED IT'S USELESS TO SAY ANYTHING. | ANGRY IMAGE | STOP, STOP. NO MORE. IT'S DANGEROUS IF THE THING IS UNCHANGED! | CRYING IMAGE | WHY NOT, I THINK OF YOU MUCH... |

FIG. 11

| CUMULATIVE QUANTITY / CHARACTER LEVEL | 0 | | 1·2·3 | | 4·5 | | 6 | |
|---|---|---|---|---|---|---|---|---|
| A) SAFE | NAPPING IMAGE | (GOODBYE. I WILL GO OUT FOR A WHILE) (I'M NAPPING SINCE I FEEL SORE) | NAPPING IMAGE | (DON'T TRY TOO HARD. TRY IN MODERATION.) (I MUST BE TIRED A LITTLE.) | RELAX IMAGE | (ANXIOUS A PERSON WHO HAS BEAUTIFUL SKIN!) (HEALTHY AND BRONZE SKIN BEAUTY!) | SMILE IMAGE | (TAKE CARE OF YOUR SKIN AFTER WASHING YOUR FACE.) |
| B) RATHER SAFE | GIVING-UP IMAGE | (TAKE CARE OF YOUR SKIN) | GIVING-UP IMAGE | (I GUESS I'M HUNGRY.) | NORMAL IMAGE | (IT ALL RIGHT TO GET SUNTANNED SOME MORE.) | LOVE IMAGE | (LA,LA,LA. FINE!) (OK! IT'S GOOD) |
| C) SLIGHTLY DANGEROUS | RELAXING IMAGE | IT'S USELESS TO SAY ANYTHING? I CANNOT MEET YOU AGAIN IF THE THING IS UNCHANGED. | RELAXING IMAGE | LET'S TAKE A REST IN THE SHADE. | SMILE IMAGE | DON'T YOU STOP TRYING IT, TODAY? | HAPPY IMAGE | YOU TRY TOO HARD? |
| D) RATHER DANGEROUS | PRESSING IMAGE | IT'S USELESS TO SAY ANYTHING? I CANNOT MEET YOU AGAIN IF THE THING IS UNCHANGED. | PRESSING IMAGE | IF YOUR SKIN IS SUNTANNED MORE, YOUR SKIN GETS SORE. | PRESSING IMAGE | IS IT ALL RIGHT TO CONTINUE SUNTAN ? | PRESSING IMAGE | MY GOD! YOUR SKIN SUNBURNS. |
| E) DANGEROUS | DISAPPOINTING IMAGE | WE ARE FINISHED, GOODBYE. | DISAPPOINTING IMAGE | OH, NO! DON'T DO THAT ANY MORE. YOUR SKIN SUNBURNS. | ANGRY IMAGE | I DO NOT GIVE YOU ADVICE ANY MORE | WARNING IMAGE | OH, NO! DON'T DO ANY MORE. |

FIG. 12

| ULTRAVIOLET RAY QUANTITY | THE NUMBER OF SUN MARKS | WARNING MESSAGE |
|---|---|---|
| 0~9mW/cm² | 1 | |
| 10~24mW/cm² | 2 | |
| 25~49mW/cm² | 3 | UV CAUTION |
| 50~mW/cm² | 4 | UV WARNING! |

PORTABLE APPARATUS AND METHOD FOR MONITORING USER'S SKIN

CROSS-REFERENCE TO RELATED APPLICATIONS

This application is based upon and claims the benefit of priority from the prior Japanese Patent Application No. 2001-026131, filed Feb. 1, 2001, the entire contents of which are incorporated herein by reference.

BACKGROUND OF THE INVENTION

1. Field of the Invention

The present invention relates to a portable apparatus, which uses a computer and which is implemented as a portable game apparatus.

2. Description of the Related Art

There are used various kinds of portable apparatuses, which are miniaturized to the degree that they can be carried with a user's hand, and the list is endless.

By the way, various kinds of portable apparatuses have been developed under the keyword of health with the crest of a recent health boom. For instance, an apparatus for measuring a percent of body fat, an apparatus for measuring skin moisture, and the like have been developed. Such portable apparatuses under the keyword of health have shaped the fixed markets, respectively.

These portable apparatuses need a sensor for directly measuring some physical quantity about user's body. In the case of measuring the user's body, an error is easily generated by an individual difference, a conditional difference and so on. Accordingly, performance of some degree is required for the sensor. For this reason, a cost problem arises quite often when such portable apparatuses are intended to be practical in use to some degree. Though the reduction in the quality of sensor can solve the cost problem, the measuring physical quantity becomes incorrect, and this is prone to have few practical applications.

On the other hand, the game apparatuses as a portable apparatus are on the market in large quantity. The dominating game apparatus in recent years is one that is configured by combining a recording medium with the game apparatus main body, namely, one in which various kinds of games can be executed by one game apparatus main body. In order to make various kinds of games implementable by one game apparatus main body, the game apparatus must have the greatest common factor in which the game apparatus main body is ready for various kinds of games. Accordingly, any game apparatus currently put on the market adopts the general configuration having input means for receiving a manual input, control means for performing predetermined control based on an operation of input means and an execution result of a program read from the recording medium, and display means for displaying a given game image under control of this control means.

Thought the portable game apparatuses have attained a huge success in terms of the market, they will tire the user if a new idea cannot be provided thereto.

The inventors of the present invention struggled for the study of the aforementioned two portable apparatuses, that is, the portable apparatus under the keyword of health and the portable game apparatus. Then, they have found out that an unconventional attractive portable apparatus can be implemented if an apparatus that has an intermediate property between both apparatus can be provided. Such a portable apparatus may not tire the user easily because of high degree of entertainment and may be excellent in the practical use.

The inventors of the present invention have also found out that the aforementioned problem relating to the measurement error due to the sensor can be solved by adopting the following configuration.

Specifically, the physical quantity about the factor that affects the user's body is measured without measuring the user's body directly, whereby predicting the user's body condition.

The adoption of such a configuration makes it possible to obtain a portable apparatus, which is in practical use in a fixed range, without using an expensive sensor and performing a special measurement.

Moreover, the inventors of the present invention have found out that an apparatus that can provide information of skin condition, which is the matter of interest to not only women but also men recently, to the user if health is used as a keyword.

The present invention explained below relates to an unconventional portable apparatus based on the aforementioned findings obtained by the inventors of the present invention.

SUMMARY OF THE INVENTION

The portable apparatus the inventors of the present invention propose is as follows. The portable apparatus of the present invention can be broadly divided into two inventions.

The first invention is as follows:

A portable apparatus of the first invention comprises measuring means for measuring a physical quantity about a factor affecting a user's skin condition to generate measurement data; controlling means for predicting a user's skin condition based on the measurement data to generate image data for displaying an image based on the prediction; displaying means for displaying an image based on the image data; and a portable housing to which the measuring means, the controlling means, and the displaying means are attached.

This portable apparatus predicts the user's skin condition and displays the image, which is based on the prediction, on the screen. Accordingly, the present invention is of practical use in providing information about the user's skin condition. This portable apparatus comprises measuring means, which is different from one, which the conventional game apparatus has. Namely, this portable apparatus comprises measuring means for measuring the physical quantity about the factor exerting an influence upon the user's skin condition to generate measurement data. Therefore, seeing this portable apparatus from the viewpoint of the portable game apparatus, this portable apparatus can provide enjoyment different from the conventional game apparatus to the user. This portable apparatus measures the physical quantity about the factor exerting an influence upon the user's body, whereby predicting the user's skin condition. In other words, this portable apparatus eliminates the need for providing a high-performance sensor since direct measurement of the user's body is not performed. This makes it possible to ensure practicality as suppressing occurrence of cost problem.

The same effect as mentioned above can be obtained by the following method.

More specifically, there is provided a method, which is executed by controlling means of a portable apparatus comprising controlling means for receiving measurement data from predetermined measuring means for measuring a physical quantity about a factor affecting a user's skin condition to generate measurement data; displaying means for displaying a predetermined image under control of the controlling means; a portable housing to which the controlling means and the displaying means are attached, the method executed by the controlling means comprising the steps of receiving the measurement data; predicting the user's skin condition based on the received measurement data; and generating image data for displaying an image, which is based on the prediction, on the display means.

Regarding controlling means, any configuration may be adopted if controlling means predicts the user's skin condition based on measurement data and generates image data for display the image, which is based on the prediction.

For example, it is possible to use controlling means comprising recording means for recording predictive data, which is data about influence exerting upon the user's skin by the factor and which is associated with the physical quantity of the factor, and extracting means for receiving the measurement data and for extracting predictive data associated with the physical quantity about the factor indicated by the measurement data, and image data generating means for generating the image data based on the predictive data extracted by the extracting means.

As mentioned above, this portable apparatus comprises measuring means different from inputting means as the conventional game apparatus has. Additionally, according to the present invention, this game apparatus may have inputting means as the conventional game apparatus has.

For example, according to the portable apparatus of the present invention, first inputting means for receiving characteristic data about a characteristic of the user's skin in a manual input to generate characteristic data may be attached to the housing. In this case, the controlling means can predict the user's skin condition based on the measurement data and the characteristic data.

Regarding controlling means of the portable apparatus having the measuring means and the first inputting means, any configuration may be possible if controlling means predicts the user's skin condition based on measurement data and characteristic data as mentioned above, and generates image data for display the image, which is based on the prediction.

The controlling means of this case can comprise recording means for recording predictive data, which is data about influence exerting upon the user's skin by the factor and which is associated with the physical quantity of the factor and the characteristic of skin, and extracting means for receiving the measurement data and the characteristic data and for extracting predictive data associated with the physical quantity about the factor indicated by the measurement data and the characteristic data, and image data generating means for generating the image data based on the predictive data extracted by the extracting means.

Regarding the physical quantity, which is measured by the measuring means, any physical quantity may be possible. For example, temperature, humidity, and the like may be measured. The measuring means can measure the ultraviolet ray quantity. The controlling means in this case can predict a degree of a suntan occurred on a user's skin as a user's skin condition.

The degree of suntan, which is based on the ultraviolet ray quantity, can be quantitatively predicted based on the ultraviolet ray quantity, which the user receives at this point or the cumulative ultraviolet ray quantity, which the user has received so far. The degree of suntan can be easily measured since this is not related to the human body. The ultraviolet ray quantity differs depending on the weather condition at this time and the location where the user is placed at this time. In the case of the portable apparatus on the assumption that the user always carries the apparatus, the ultraviolet ray quantity can be relatively easily measured, and it is not so difficult to perform continuous measurement even if the ultraviolet ray quantity changes every moment. Accordingly, this measuring apparatus can provide information, which the user desires, relatively correctly with a relatively simple configuration.

The controlling of this case can be configured as follows. Namely, it is possible to use controlling means comprising recording means for recording predictive data, which is data about a degree of the suntan occurred on the user's skin with ultraviolet rays and which is associated with the ultraviolet ray quantity and the characteristic of the user's skin, and extracting means for receiving the measurement data and for extracting predictive data associated with the ultraviolet ray quantity indicated by the measurement data, and image data generating means for generating the image data based on the predictive data extracted by the extracting means.

The first inputting means of this case may receive the characteristic of user's skin against the suntan as the characteristic data, and the controlling means may predict the degree of user's suntanned skin as a user's skin condition.

The measuring means of this case is the ultraviolet sensor for measuring the ultraviolet ray quantity as the physical quantity, the first inputting means can receive the characteristic of user's skin against the suntan as the characteristic data, and the controlling means can predict the degree of user's suntanned skin as a user's skin condition.

The controlling of this case can comprise recording means for recording predictive data, which is data about a degree of the suntan occurred on the user's skin with ultraviolet rays and which is associated with the ultraviolet ray quantity and the characteristic of the user's skin, and extracting means for receiving the measurement data and the characteristic data and for extracting predictive data associated with the ultraviolet ray quantity indicated by the measurement data and the characteristic of the skin indicated by the characteristic data, and image data generating means for generating the image data based on the predictive data extracted by the extracting means.

Additionally, measuring means may be combined with the housing or separated therefrom. In the latter case, the portable apparatus results in a portable apparatus comprising controlling means for receiving measurement data from predetermined measuring means for measuring a physical quantity about a factor affecting a user's skin condition to generate measurement data, for predicting a user's skin condition based on the received measurement data, and for generating image data for displaying an image based on the prediction; displaying means for displaying an image based on the image data; and a portable housing to which the measuring means, the controlling means, and the displaying means are attached.

In the case where the measuring means measures ultraviolet rays, it is possible to use an ultraviolet sensor, which measures an ultraviolet ray quantity to generate measurement data about the ultraviolet ray quantity, as the measuring means. The portable apparatus of this case is as follows.

Namely, this is a portable apparatus comprising an ultraviolet sensor for measuring an ultraviolet ray quantity to generate measurement data about the ultraviolet ray quantity; first inputting means for receiving characteristic data about a characteristic of a user's skin against a suntan in a manual input; controlling means for predicting a user's suntanned skin condition based on the measurement data and the characteristic data to generate image data for displaying an image about the prediction of the user's suntanned skin condition based on the prediction; displaying means for displaying the image about the prediction of the user's suntanned skin condition based on the image data; and a portable housing to which the ultraviolet sensor, the controlling means, and the displaying means are attached.

The controlling means can comprises recording means for recording predictive data, which is data about a degree of the suntan occurred on the user's skin with ultraviolet rays and which is associated with the ultraviolet ray quantity and the characteristic of the user's skin, and extracting means for receiving the measurement data and the characteristic data and for extracting predictive data associated with the ultraviolet ray quantity indicated by the measurement data and the characteristic of the skin indicated by the characteristic data, and image data generating means for generating the image data based on the predictive data extracted by the extracting means.

The controlling means may calculate cumulative data about a cumulative ultraviolet ray quantity, which is a cumulative value of the ultraviolet ray quantities after the start of measurement based on measurement data sequentially received after the start of measurement. Then, the controlling means may predict the user's suntanned skin condition based on the cumulative data and the characteristic data. The use of the concept of the cumulative ultraviolet ray makes it possible to predict the user's skin condition using continuous measurement data about the past. This makes it possible for the user to continuously obtain reliable and effective information. The accumulation of ultraviolet rays may be calculated by measurement of continuous ultraviolet ray quantity or that of periodical ultraviolet ray quantity.

The portable apparatus of the present invention may comprise second inputting means for receiving desirable data about a user's suntan desire as to which the user desires promotion of a suntan or protection of suntan. The controlling means may predict a user's suntanned skin condition based on the measurement data and the characteristic data, reflects the user's suntan desire based on the prediction and the characteristic data, and generates image data for displaying an image, which is based on the prediction of the user's suntanned skin condition, on the display device.

This makes it possible to provide appropriate information to the user in order to obtain the suntanned skin, which the user desires.

The portable apparatus of the present invention may comprise second inputting means for receiving desirable data about a user's suntan desire as to which the user desires promotion of a suntan or protection of suntan. The controlling means may predict a user's suntanned skin condition based on the cumulative data and the characteristic data, reflects the user's suntan desire based on the prediction and the desirable data, and generates image data for displaying an image, which is based on the prediction of the user's suntanned skin condition, on the display device.

The portable apparatus of the present invention may comprise third inputting means for receiving sun protection data about means for protecting the suntan used by the user. The controlling means may predict the user's suntanned skin condition based on the measurement data, the characteristic data, and the sun protection data, and generates the image data based on the prediction and the desirable data.

Or, the portable apparatus of the present invention may comprise third inputting means for receiving sun protection data about means for protecting the suntan used by the user, wherein the controlling means predicts the user's suntanned skin condition based on the cumulative data, the characteristic data, and the sun protection data, and generates the image data based on the prediction and the desirable data.

The present invention is embodied as a method, which is executed by controlling means of a portable apparatus comprising controlling means for receiving measurement data from a predetermined ultraviolet sensor for measuring an ultraviolet ray quantity to generate measurement data about the ultraviolet ray quantity; displaying means for displaying a predetermined image under control of the controlling means; a portable housing to which the controlling means and the displaying means are attached, the method executed by the controlling means comprising the steps of:

receiving the measurement data; predicting the user's skin condition based on the received measurement data; and generating image data for displaying an image, which is based on the prediction, on the display means.

The first, second, and third inputting means may be separately provided, or two or all of them may be combined as one body.

The second invention is as follows:

A portable apparatus of the second invention comprises an ultraviolet sensor for measuring an ultraviolet ray quantity to generate measurement data about the ultraviolet ray quantity; first inputting means for receiving characteristic data about a characteristic of a user's skin against a suntan in a manual input; reference setting means for receiving the characteristic data and for setting a reference ultraviolet ray quantity, which is the ultraviolet ray quantity judged as being dangerous to a user; warning means for receiving the measurement data, for determining whether or not the ultraviolet ray quantity indicated by the measurement data exceeds the reference ultraviolet ray quantity, and when the ultraviolet ray quantity indicated by the measurement data exceeds the reference ultraviolet ray quantity, for generating image data for displaying an image indicating the excess of the ultraviolet ray quantity; displaying means for displaying an image indicating a warning that a current ultraviolet ray quantity is harmful to the user based on the image data; and a portable housing to which the ultraviolet sensor, the reference setting means, the warning means, and the displaying means are attached.

When the reference ultraviolet ray quantity set based on characteristic information inputted by the user is used as a threshold value and the ultraviolet ray quantity, which exceeds this, exists around the user, this portable apparatus informs the user of this matter. This makes it possible for the user to know the ultraviolet ray quantity at the present time and location relatively easily.

Moreover, the same function and effect can be obtained by a method, which is executed by controlling means of a portable apparatus comprising an ultraviolet sensor for measuring an ultraviolet ray quantity to generate measurement data about the ultraviolet ray quantity; first inputting means for receiving characteristic data about a characteristic of a user's skin against a suntan in a manual input; controlling means for receiving the measurement data and the characteristic data to generate predetermined image data based on these data; displaying means for displaying a predetermined image based on the image data; and a portable housing to which the ultraviolet sensor, the reference setting means, the warning means, and the displaying means are attached, the method executed by the controlling means comprising the steps of:

receiving the characteristic data to set a reference ultraviolet ray quantity, which is the ultraviolet quantity judged as being dangerous to a user; receiving the measurement data to determine whether or not the ultraviolet ray quantity indicated by the measurement data exceeds the reference ultraviolet ray quantity; and generating image data, when the ultraviolet ray quantity indicated by the measurement data exceeds the reference ultraviolet ray quantity, for displaying an image indicating the excess of the ultraviolet ray quantity. The reference setting means of the above portable apparatus may be one that sets the reference ultraviolet ray without being based on specific data, for example, one that presets the quantity.

This portable apparatus may have third inputting means similar to the first invention. The portable apparatus of this case is the aforementioned portable apparatus further comprising third inputting means for receiving sun protection data about means for protecting the suntan used by the user, wherein the reference setting means sets the reference ultraviolet ray quantity based on the characteristic data, and the sun protection data.

Additionally, the ultraviolet sensor may be combined with the housing or may be separately provided. The portable apparatus of the latter case results in a portable apparatus comprising an ultraviolet sensor for measuring an ultraviolet ray quantity to generate measurement data about the ultraviolet ray quantity; reference setting means for setting a reference ultraviolet ray quantity, which is the ultraviolet quantity judged as being dangerous to a user; warning means for receiving the measurement data, for determining whether or not the ultraviolet ray quantity indicated by the measurement data exceeds the reference ultraviolet ray quantity, and when the ultraviolet ray quantity indicated by the measurement data exceeds the reference ultraviolet ray quantity, for generating image data for displaying an image indicating the excess of the ultraviolet ray quantity; displaying means for displaying an image indicating a warning that a current ultraviolet ray quantity is harmful to the user based on the image data; and a portable housing to which the ultraviolet sensor, the reference setting means, the warning means, and the displaying means are attached.

BRIEF DESCRIPTION OF THE DRAWINGS

These objects and other objects and advantages of the present invention will become more apparent upon reading of the following detailed description and the accompanying drawings in which:

FIG. 6 is a view conceptually illustrating an example of basic data;

FIG. 7A is a view illustrating an example of an image displayed on a display of the portable apparatus illustrated in FIG. 1;

FIG. 7B is a view illustrating an example of an image displayed in the image of FIG. 7A;

FIG. 10 is a view conceptually illustrating the contents of a table for determining an image displayed on a display device;

FIG. 11 is a view conceptually illustrating the contents of a table for determining an image displayed on the display device; and FIG. 12 is a view explaining the way to determine a reference ultraviolet quantity.

DETAILED DESCRIPTION OF THE PREFERRED EMBODIMENT

An embodiment of the present invention will be specifically described with reference to the drawings accompanying herewith. This apparatus is as illustrated in, for example, FIG. 1.

Figure 1:
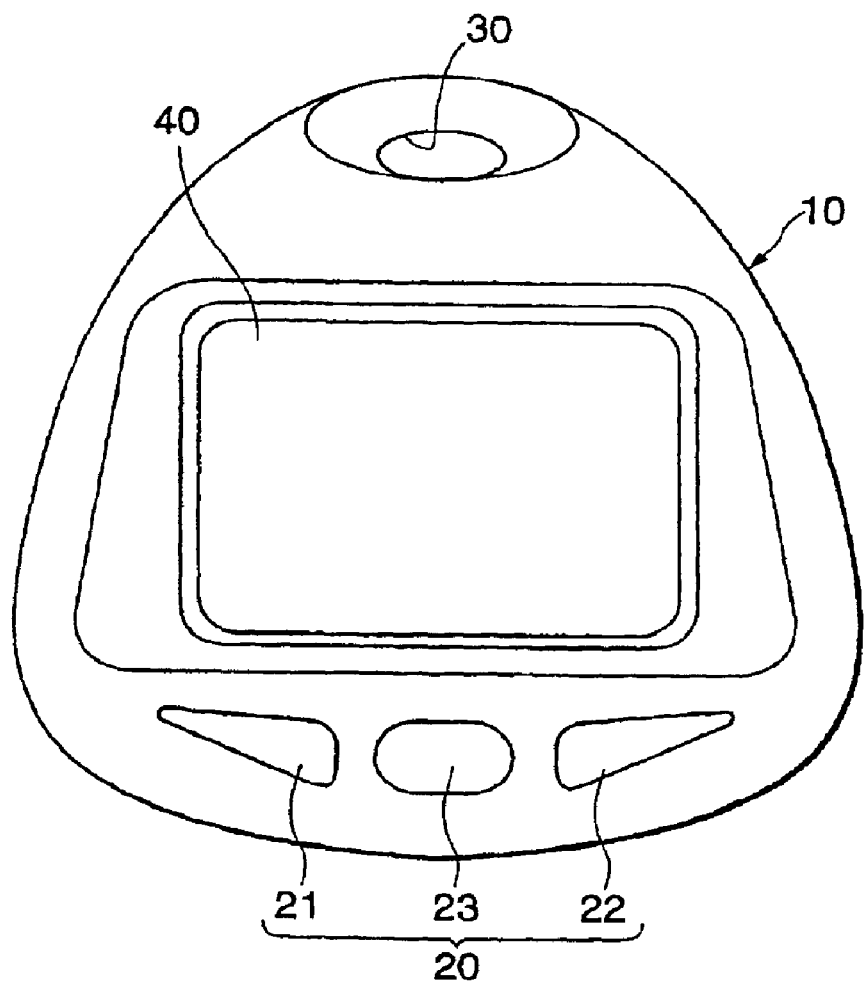
FIG. 1 is an oblique perspective figure illustrating an outline of a portable apparatus according to one embodiment of the present invention.

This apparatus, as illustrated in FIG. 1, has a configuration in which an input key 20, an ultraviolet receptive opening 30 and a display 40 are combined with a housing 10 as one body. The housing 10 also has a circuit (not shown) for controlling the portable apparatus built in.

The housing 10 is made of, for example, resin, Moreover, the housing 10 is shaped small to a degree that it can be grasped with a user's hand and is shaped overly in such a way to be easily gasped with the user's hand.

The input key 20 is provided at a lower front surface of the housing 10, and is composed of a left input key 21, a right input key 22, and a central input key 23. The input key 20 serves as first input means, second input means, and third input means of the present invention. From the input key 20, it is possible to input at least characteristic data about a characteristic of user's skin against suntan, desirable data about user's desire for suntan on which of the promotion of suntan and the protection of suntan the user desires, and sun protection data about means for protecting suntan used by the user. The left input key 21 and the right input key 22 function as a command selection key, and the central key 23 functions as a command decision key. The operation method at the time of input will be described later.

The ultraviolet receptive opening 30 is an opening for guiding light from the outer unit to the interior of the housing 10. In the interior of the housing 10 of the ultraviolet receptive opening 30, an ultraviolet sensor (not shown) corresponding to measuring means of the present invention is provided, so that the quantity of ultraviolet rays in the light received through the ultraviolet receptive opening 30 can be detected. As a result, the ultraviolet sensor generates measuring data, which is data about the quantity of ultraviolet rays. The ultraviolet sensor may be configured as a photo-diode in which a GaAsP chip and the ultraviolet sensor are combined without being limited to this. More specifically, G5842 made by Hamamatsu Photonics K.K. can be used as an ultraviolet sensor in this embodiment. Additionally, a film having a moisture-proof function may be adhered on the surface (light-receptive surface facing to the ultraviolet opening 30) of the ultraviolet sensor. In addition, the ultraviolet sensor may be attached and detached to and from the housing 10. If the normal portable game apparatus has some input terminal, the terminal and the ultraviolet sensor may be connected to each other.

The display 40 corresponds to display means of the present invention. The display 40 is composed of, e.g., a liquid crystal display of a dot-matrix type, and a portion provided to the user is substantially rectangularly shaped.

Figure 2:
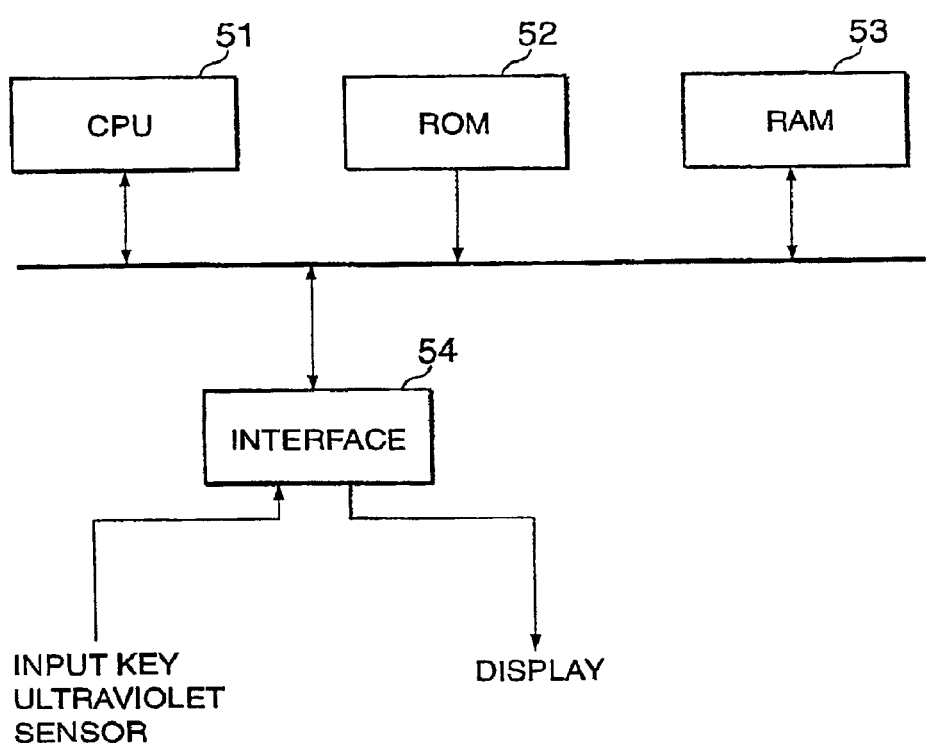
FIG. 2 is an internal configuration view of the portable apparatus illustrated in FIG. 1.

A circuit provided in the interior of the portable apparatus is as illustrated in, for example, FIG. 2. This circuit includes a CPU (Central Processing Unit) 51, ROM (Read Only Memory) 52, RAM (Random Access Memory) 53, and an interface 54. Then, ROM 52, RAM 53, and interface 54 are connected to the CPU 51 via a bus.

The CPU 51 executes predetermined processing by executing a predetermined program. ROM 52 stores a program for operating the CPU 51, prediction data, which is necessary when the presentation of data based on the prediction of skin condition to be described later, image data, which is used when the image is displayed on the display 40, and the like. RAM 53 provides a work area where CPU performs data processing. The interface 54 functions as a connection circuit for input and output of CPU 51. The input key 20, ultraviolet sensor, display 40 are connected to the CPU 51 via the interface 54. Input data generated by the operation of input key 20 and measured data generated by the ultraviolet sensor is inputted to the CPU 51 via the interface 54. Image information generated by the CPU Si is outputted on the display 40 via the interface 54. The display 40 performs display based on this information.

Figure 3:
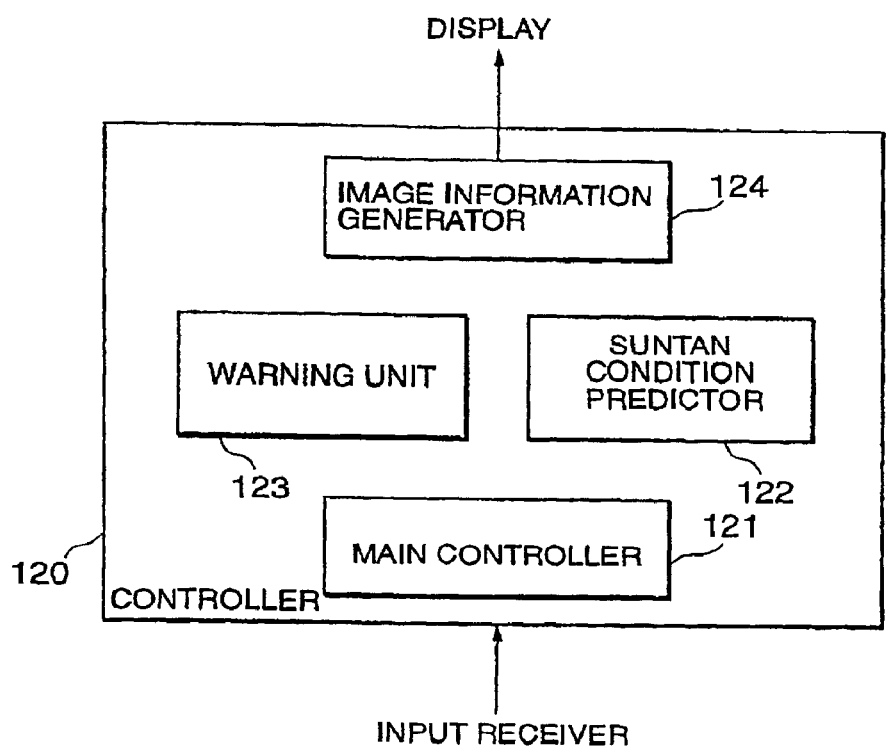
FIG. 3 is a view illustrating a function block generated in the portable apparatus illustrated in FIG. 1.
Figure 4:
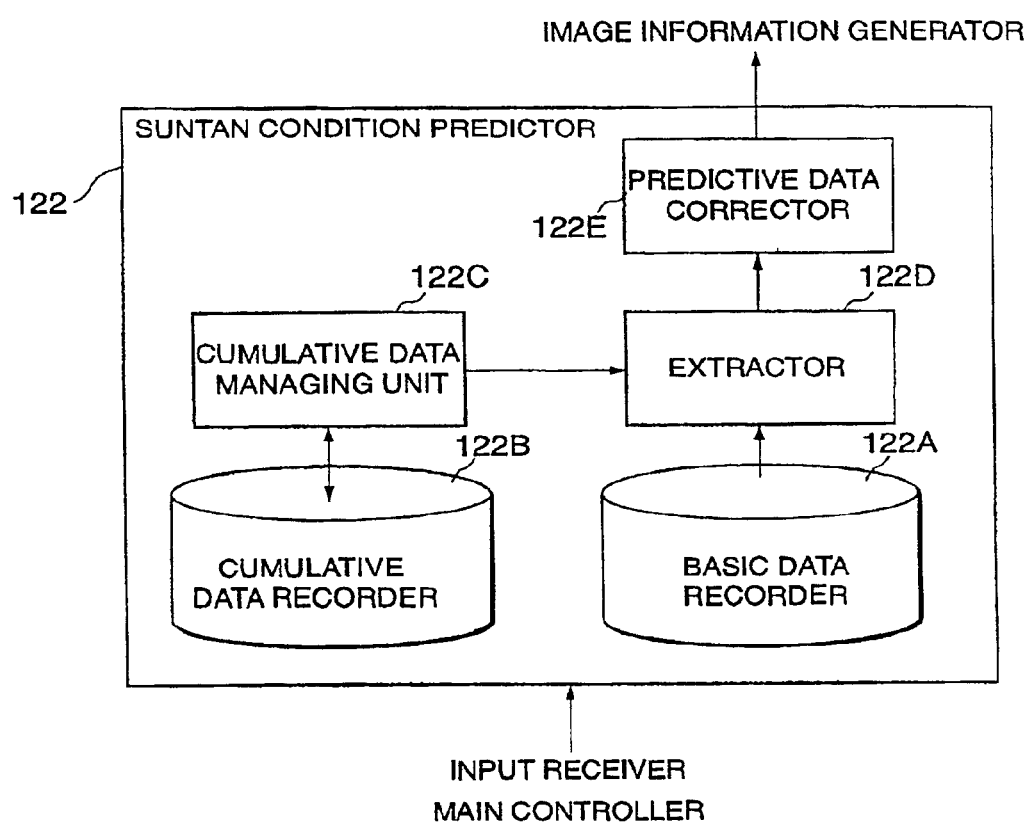
FIG. 4 is a block diagram illustrating the configuration of a controller of FIG. 3.

In this portable apparatus, the function block as illustrated in FIG. 3 is generated in its interior by executing the aforementioned program by the CPU 51 at the time when power is turned on or a predetermined reset operation is performed.

This portable apparatus comprises an input receiver 110 and a controller 120.

The input receiver 110 has a function of receiving data inputted from the input key 20 or the ultraviolet sensor to transmit data to the controller 120.

The controller 120 corresponds to control means of the present invention, and controls the entirety of the portable apparatus. Moreover, the controller 120 executes the presentation of information based on the prediction of skin condition and processing for giving a warning to the user based on an increase in the quantity of ultraviolet rays. The controller 120 also generates image data for displaying a given image on the display device based on the processing result.

The controller 120 comprises a main controller 121, a suntan condition predictor 122, a warning unit 123, and an image generator 124 in its interior.

The main controller 121 controls the suntan condition predictor 122, the warning unit 123, and the image generator 124 based on information from the input key 20, For example, the main controller 121 instructs the suntan condition predictor 122 and the warning unit 123 to perform predetermined processing, or generates information for stopping based on information from the input key 20 via the input receiver 110 and sends the generated information to the suntan condition predictor 122 and the warning unit 123. In order to generate image data for displaying a given image (for example, such a moving image of a character that interests the user) on the display 40, the main controller 121 performs control of a setting mode to be described later. In this case, the main controller 121 sends data about a command of that purpose to an image data generator 124.

The suntan condition predictor 122 exerts a function as a controller of the present invention in combination with the image data controller 124. The suntan condition predictor 122 predicts the user's skin condition based on information received from the main controller 121 and information received from the input key 20 and the ultraviolet sensor via the input receiver 110 (in this embodiment, the user's suntanned skin condition is predicted). The suntan condition predictor 122 also generates predictive data based on the prediction result. Predictive data is sent to the image data controller 124.

The warning unit 123 exerts a function as warning means of the present invention in combination with the image data controller 124. The warning unit 123 sets a reference ultraviolet ray quantity, which is the ultraviolet ray quantity determined as being harmful to the user, based on information received from the main controller 121 and information received from the input key 20 and the ultraviolet sensor via the input receiver 110. Then, the warning unit 123 determines whether or not the ultraviolet ray quantity at this time exceeds the reference ultraviolet ray quantity. In the case where the ultraviolet ray quantity indicated by measured data exceeds a threshold value as a result of the determination, the warning unit 123 generates warning data for displaying an image indicative of that point. Warning data is sent to the image data controller 124.

The image data generator 124 receives predictive data from the suntan condition predictor 122, warning data from the warning unit 123, or predetermined data from the main controller 121. Then, the image data generator 124 generates image data for displaying a predetermined image on the display 40 based on these data. Image data is sent to the display 40. As a result, the image, which is based on sent data, is displayed on the display device.

The suntan condition predictor 122 is configured to include a basic data recorder 122A, a cumulative data recorder 122B, a cumulative data managing unit 122C, an extractor 122D, and a predictive data corrector 122E.

On the basic data recorder 122A, basic data, which is data about the degree of suntan generated on the human skin with the ultraviolet rays. Basic data is one that is statistically obtained in connection with an influence that the ultraviolet rays exert upon the human skin. In this embodiment, basic is set in connection with the ultraviolet ray quantity. The basic data in this example is associated with not only the ultraviolet rays but also human skin properties though the basic data is not limited to this. Additionally, the ultraviolet ray quantity is set to the cumulative ultraviolet ray quantity obtained by accumulating the ultraviolet ray quantity measured at a predetermined time interval (every one minute in this embodiment).

More specifically, on the basic data recorder 122A in this example, first basic data and second basic data as illustrated in FIG. 6 are recorded. They are divided according to the kinds of desirable data inputted by the user as described later.

Both first basic data and second basic data refer to the prediction of the skin conditions including five predictive data (described as predictions in FIG. 6), namely, A) safe, B) rather safe, C) slightly dangerous D) rather dangerous, and E) dangerous. They are associated with the skin level (to be described later) and the cumulative ultraviolet ray quantity (indicated by ~10 kJ/m$^2$, ~40 kJ/m$^2$, and the like), respectively. For example, in the case of using the first data, when the skin level is 3 and the cumulative ultraviolet ray quantity is ~43 kJ/m$^2$, predictive data becomes C). In the case of using the second data, when the skin level is 1 and the cumulative ultraviolet ray quantity is ~55 kJ/m$^2$, predictive data becomes E).

The cumulative data recorder 122B records the cumulative ultraviolet ray quantity. In this embodiment, the aforementioned ultraviolet sensor is designed to measure the ultraviolet ray quantity every one minute. The cumulative data recorder 122B records the ultraviolet ray quantity (unit; $kJ/m^2$) obtained by the measured ultraviolet ray quantity one minute based on received measured data. Additionally, control of ultraviolet sensor that performs measurement every one minute can be carried out by, for example, the main controller 121.

The cumulative data managing unit 122C performs management of data (cumulative data) about the cumulative ultraviolet ray quantity recorded on the cumulative data recorder 122B. Recording cumulative data onto the cumulative data recorder 122B is carried out by the cumulative data managing unit 122C. The cumulative data managing unit 122C reads cumulative data from the cumulative data recorder 122B as required and sends it to the extractor 122D.

The extractor 122D extracts characteristic data, which is generated when the user inputs the input key 20 and which is inputted via an input information analyzer 110, and predictive data from basic data based on the aforementioned cumulative data. The way to extract predictive data will be described later. At the time of extracting predictive data, desirable data, which is generated when the user inputs the input key 20 and which is inputted via the input analyzer 110, is also used, and this will be described later.

The predictive information corrector 122E adds a predetermined correction to predictive data received from the extractor 122D. At the time of this change, protection data, which is generated when the user inputs the input key 20 and which is inputted via the input analyzer 110, is also used, and this will be described later.

Figure 5:
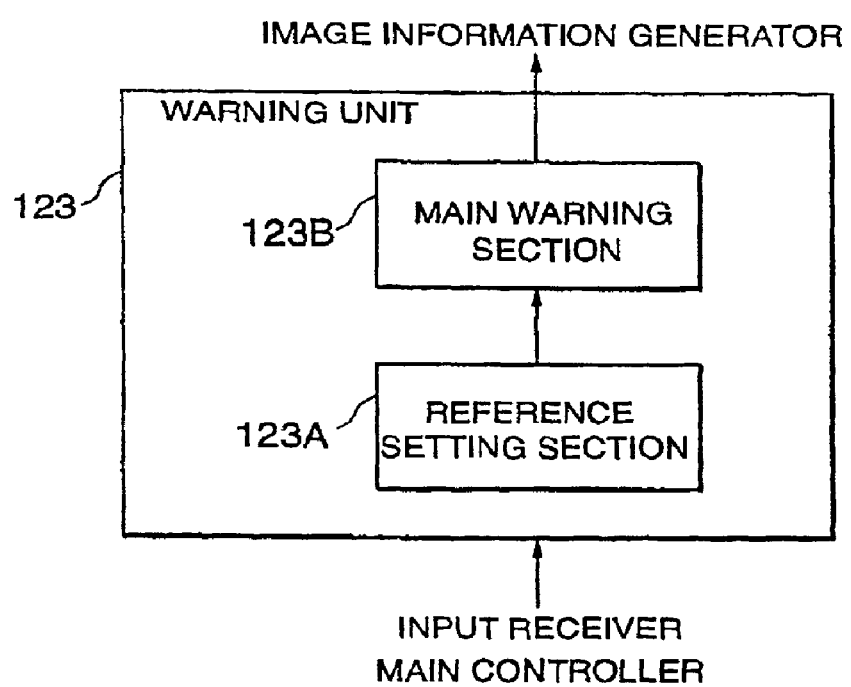
FIG. 5 is a block diagram illustrating the configuration of a warning unit of FIG. 3.

The warning unit 123 is composed of a reference setting section 123A and a main warning section 123B as illustrated in FIG. 5.

The reference setting section 123A corresponds to reference setting means of the present invention, and sets a reference ultraviolet ray quantity, which is the ultraviolet ray quantity judged as being dangerous to the user. The reference ultraviolet ray quantity in this example means the ultraviolet ray quantity at a certain point. In the portable apparatus of this embodiment, the reference setting section 123A generates reference data based on characteristic data about the characteristic of user's skin against suntan. The generated reference data is sent to the main warning section 123B.

The main warning section 123B receives measured data from the input key 20 operated by the user via the receiver 110. The main warning section 123B also determines whether or not the ultraviolet ray quantity indicated by measured data exceeds the reference ultraviolet ray quantity. In the case where the ultraviolet ray quantity indicated by the measured data exceeds the reference ultraviolet ray quantity indicated by the reference data, the main warning section 123B generates image data about a displaying image indicative of this fact, e.g., such an image that gives warning to the user. Warning data generated by the main warning section 123B is sent to the image information generator 124.

An explanation will be next given of the method of the present invention by explaining the using method of this portable apparatus and the operation.

This portable apparatus automatically displays a start-up screen page on the display 40 when power is turned on. The image is displayed based on image data generated by the image information generator 124 under control of the main controller 121.

On the start-up screen page, the logo of a company that manufactures the portable apparatus and a title logo can be displayed. One that introduces a character appearing on this portable apparatus may be displayed on the start-up screen page. Since this portable apparatus uses the character of a bear, the logo of the company is displayed and the title logo is displayed by scrolling and the moving image for introducing the character is sequentially displayed on the start-up screen page.

After displaying the start-up screen page, initial setting modes are automatically executed. The initial setting modes, each processing of time adjustment, skin level setting, and suntan selection is automatically executed. Control of executing the above processing is carried out by, e.g., the main controller 121.

In the initial setting modes, inputs necessary for each processing of time adjustment, skin level setting, and suntan selection are performed using the input key 20.

The time adjusting mode is executed in order of "hour" and "minute."

First, any number from 0 to 24 indicating "hour" is displayed on the display 40. The user operates the left input key 21 and the right input key 22 suitably, and changes the number. Though the present invention is not limited to this, in this embodiment, when the left input key 21 is depressed, the number is decreased by one each time. When the right input key 22 is depressed, the number is increased by one each time. The numbers 0 and 24 may be looped to be continued. When the displayed number adjusts to the current "hour", the central input key 23 is depressed, thereby setting the "hour."

Next, any number from 0 to 60 indicating "minute" is displayed on the display 40. The user operates the left input key 21 and the right input key 22 suitably, and changes the number. The numbers 0 and 60 may be looped to be continued. Though the present invention is not limited to this, in this embodiment, when the left input key 21 is depressed, the number is decreased by one each time. When the right input key 22 is depressed, the number is increased by one each time. When the displayed number adjusts to the current "minute", the central input key 23 is depressed, thereby setting the "minute."

Thus, the time adjustment is ended.

After that, the skin level setting level is executed.

At the time of setting the skin level, the screen page as illustrated in, for example, FIG. 7A is displayed. This screen page is composed of a rectangular skin level numeral value displaying section (indicated by 1 in FIG. 7A) formed by cutting the upper right portion on the screen page, a skin level displaying section formed thereunder (indicated by "yowai" (Japanese transliteration) meaning "delicate" in FIG. 7A), an explanation displaying section formed thereunder (indicated by "sugu" (Japanese transliteration) meaning "soon" in FIG. 7A), and a character displaying section formed at the lowest portion (the upper half of the face of the bear is displayed in FIG. 7A).

The skin level numeral value displaying section is a part that displays one obtained by converting the characteristic of skin into number. The numeral value in this example indicates the point in which the larger the numeral value is, the stronger against suntan the skin is.

The skin level displaying section displays the characteristic of skin. Namely, the skin level displaying section displays the character representing the characteristic of skin against suntan, specifically any one of "delicate", "rather delicate", "normal", "rather strong", and "strong."

The explanation displaying section displays the specific content of the characters displayed on the skin level displaying section. More specifically, any one of "the skin becomes red-hot soon and no suntanned" "the skin becomes red-hot easily and no suntanned easily", "the skin becomes red-hot first, but suntanned gradually" "the skin becomes little red-hot and suntanned well" and "the skin does not become red-hot and suntanned easily." is displayed. These characters are automatically scrolled horizontally. This makes it possible for the user to confirm the entire sentence.

The numeral value displayed on the skin level numeral value displaying section, the character displayed on the skin level displaying section, and the character displayed on the explanation displaying section are associated with one another as illustrated in FIG. 7B.

The user operates the input key 20, and selects the skin level numeral value corresponding to the user's skin level. When the user depresses the left input key 21 or the right input key 22, the numeral value displayed on the skin level numeral value displaying section, the character displayed on the skin level displaying section, and the character displayed on the explanation displaying section change appropriately as keeping the relationship therebetween. In the portable apparatus of this embodiment, when the left input key 21 is depressed, the number displayed on the skin level numeral value displaying section is decreased by one each time. Moreover, when the right input key 22 is depressed, the number displayed on the skin level numeral value displaying section is increased by one each time. The loop may be formed as mentioned above. When the skin level corresponding to the characteristic of user's skin is displayed, the user depresses the central input key 23. This generates characteristic data about the characteristic of the user's skin against suntan, This characteristic data is sent to the controller 120 via the input receiver 110.

After displaying the start-up screen page, initial setting modes are automatically executed. The initial setting modes, each processing of time adjustment, skin level setting, and suntan selection is automatically executed. Control of executing the above processing is carried out by, e.g., the main controller 121.

In the initial setting modes, inputs necessary for each processing of time adjustment, skin level setting, and suntan selection are performed using the input key 20.

The suntan selection mode is next executed.

The suntan selection mode is one that asks the user about the user's desire of suntan, namely, the user desires to get suntanned positively or protect the suntan as possible.

Figure 8A:
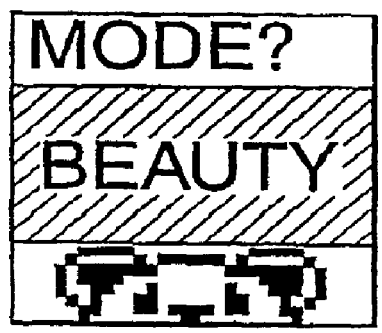
FIG. 8 is a view illustrating an example of an image displayed on a display of the portable apparatus illustrated in FIG. 1.
Figure 8B:
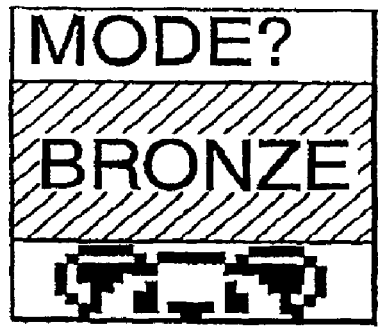

When this mode is started, one of images as illustrated in FIG. 8A and FIG. 8B is displayed. The image illustrated in FIG. 8A indicates that a beauty mode is selected as shown by the character of the middle portion when the central input key 23 is depressed while the image is being displaying. The image illustrated in FIG. 8B indicates that a bronze mode is selected as shown by the character of the middle portion when the central input key 23 is depressed while the image is being displaying. The beauty mode indicates that the user wishes to protect the suntan as possible, and the bronze mode indicates the user wishes to get suntanned beautifully. As illustrated in FIG. 6, in the beauty mode, first basic mode is selected in the beauty mode and second basic mode is selected in the bronze mode. This reflects the user's desire.

The user operates the left input key 21 and the right input key 22 appropriately to change the image illustrated in FIG. 8A and FIG. 8B.

Though the present invention is not limited to this, in this embodiment, when the left input key 21 or the right input key 22 is depressed, the image illustrated in FIG. 8A and the image illustrated in FIG. 8B are changed each time.

When the favorable image is displayed, the user depresses the central key 23. This generates desirable data about the user's desire of suntan, namely the user desires the promotion of suntan or the protection of suntan. Desirable data is sent to the controller 120 via the input receiver 110.

The initial setting modes are thus ended.

After that, the portable apparatus is put into normal mode in which processing for displaying the image about the prediction of user's suntanned skin condition and processing for warning that the ultraviolet ray quantity is harmful to the user at this point are executed in parallel.

In the normal mode, a suitable mode can be selected from a time display mode, an ultraviolet ray quantity real time display mode, an ultraviolet ray cumulative quantity display mode, and a setting mode by the operation of the input key 20. These modes are looped as illustrated in, for example, FIG. 9. In this embodiment, when the right input key is depressed, the selective candidate is changed clockwise. When the left input key is depressed, the selective candidate is changed half-clockwise. Also, the image corresponding to each mode is displayed as illustrated in the figure. The user has only to depress the central input key 23 while the image corresponding to the mode, which the user wishes to select, is displayed, whereby the mode is selected. Additionally, control of the mode selection is carried out by the main controller 121.

The contents of the time display mode, the ultraviolet ray quantity real time display mode, the ultraviolet ray cumulative quantity display mode, and the setting mode are explained as follows.

Figure 9:
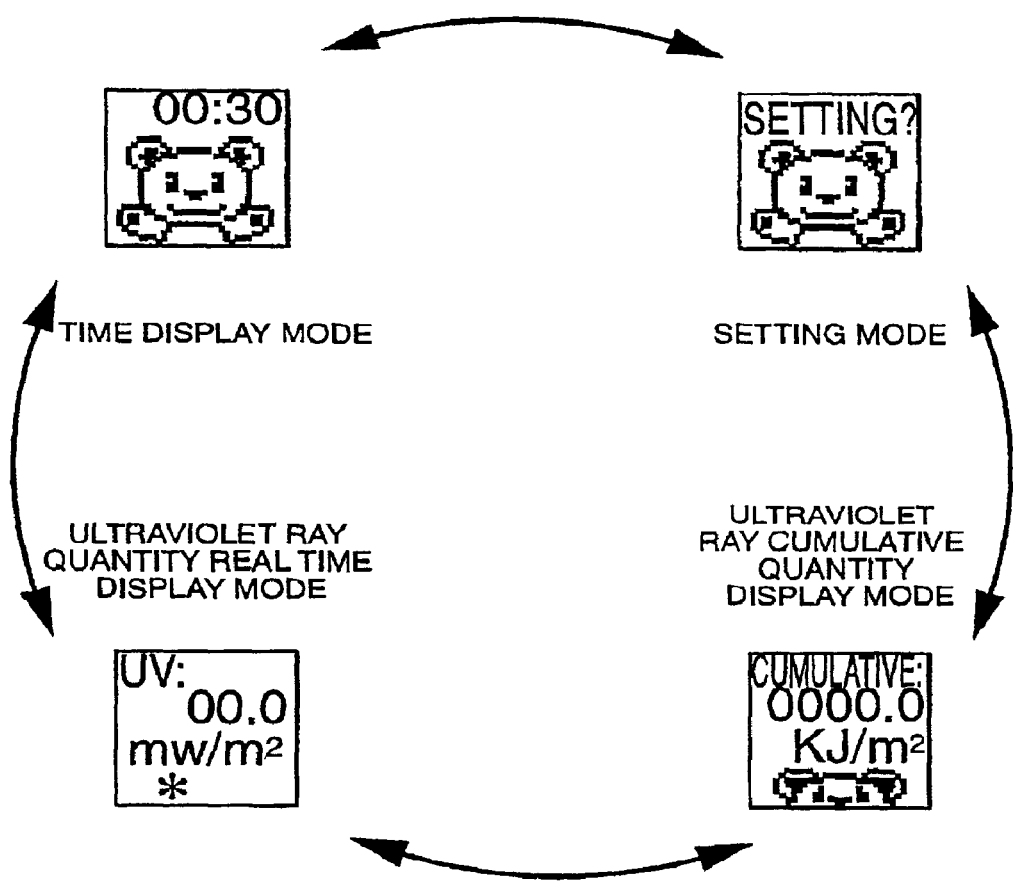
FIG. 9 is a view illustrating an example of a mode selectable in a normal mode.

More specifically, the time display mode is designed to display the time at this point. In FIG. 9, 00:30 is indicated.

The ultraviolet ray quantity real time display mode is designed to display the ultraviolet ray quantity at this point (to be more precise, the latest value among the measurement values of the ultraviolet ray quantity measured every one minute). The unit is $mW/cm^2$.

The ultraviolet ray cumulative quantity display mode is designed to display the ultraviolet ray cumulative quantities accumulated so far after power-on (after the resetting in the case where the resetting has been performed). The unit is $kJ/m^2$. At the time of performing this display, cumulative data read from the cumulative data recorder 122B by the data managing section 122C is used. For example, the main controller 121, which has received this data, sends the data to the image data generator 124, whereby generating image data for displaying the image as illustrated in FIG. 9.

The setting mode is designed to rekey the aforementioned characteristic data and input sun protection data. Screen lightness setting may be performed. Moreover, in the case where this portable apparatus has a speaker for outputting a predetermined effect sound, a sound ON/OFF setting, a volume setting and the like may be performed.

The mode selection in the setting mode is carried out using the input key 20 similar to the aforementioned case. Sun protection data, which can be input in the setting mode, is data about means for protecting suntan, which is used by the user.

In this embodiment, when the user uses a sunscreen such as sun protection cream, SPF (Sun Protection Factor) value (suntan time (human skin is actually measured)/suntan time that elapses before the skin becomes slightly red-hot when no sunscreen is applied) is inputted. Whereby, entry of sun protection data is performed. On the screen page for instructing the user to input sun protection data, numeral values 0 to 50 are displayed on the display 40. Similar to the case of time adjustment, the user depresses the left input key 21 and the right input key 22 to increase and decrease the aforementioned number, and depresses the central input key 23, whereby the entry of sun protection data is made. The number (SPF value of the sunscreen used by the user) displayed when the central input key 23 becomes sun protection data. This data is inputted to the predictive information corrector 122E via the input receiver 110.

When the portable apparatus is placed in the normal mode, the ultraviolet sensor performs the measurement of ultraviolet ray quantity as mentioned above. Measurement data generated thereby is sent to the controller 120 via the input receiver 110. Then, processing for displaying the image about the prediction of user's suntanned skin condition and processing for warning that the ultraviolet ray quantity is harmful to the user at this point are executed in parallel by use of this measurement data. The following will explain both processing in order.

An explanation will be first given of processing for displaying the image about the prediction of user's suntanned skin condition. This processing is mainly carried out by the suntan condition predictor 122.

Measurement data sent to the controller 120 is sent to the cumulative data controlling section 122C provided in the suntan condition predictor 122. The cumulative data controlling section 122C calculates cumulative data about the cumulative ultraviolet ray quantities, which is the cumulative value of ultraviolet ray quantities obtained after the start of measurement, based on measurement data sequentially received after the start of measurement. Then, the cumulative data controlling section 122C writes the calculation result to the cumulative data recorder 122B. Additionally, cumulative data is reset to 0 at 00:00 A.M.

On the other hand, the extractor 122D reads cumulative data from the cumulative data recorder 122B via the cumulative data managing section 122C. Then, the extractor 122D reads basic data from the basic data recorder 122, and generates predictive data based on cumulative data, basic data, and characteristic data previously received.

Basic data to be read by the extractor 122D is determined based on desirable data, which is received by the extractor 122D through the input receiver 110. Namely, in the case where desirable data indicates that the mode selected by the user is the beauty mode, first basic data is selected. In the case where desirable data indicates that the mode selected by the user is the bronze mode, second basic data is selected.

Predictive data is determined based on the skin level and the cumulative ultraviolet ray quantity. The way to determine predictive data has been already described in the explanation of FIG. 6. Measurement data is sent to the cumulative data recorder 122B. Predictive information is sent to the predictive information corrector 122E.

The predictive information corrector 122B is designed to add correction to received predictive information as required. This correction is performed based on protection data, which the predictive information corrector 122E has received.

Sun protection data is the SPF value of sunscreen, which the user employs as mentioned above. Then, sun protection data is reduced with a lapse of time. In this embodiment, in the case where sun protection data is left, a change is made to predictive data. For example, predictive data can be decreased by one level, e.g., from E) to A) or from B) to A).

In the case where sun protection data indicates that the sunscreen is not used from the beginning or is reduced to 0, predictive data is maintained as it is, and the predictive information corrector 122B sends predictive information to the image generator 124, directly. Additionally, the SPF value shown by sun protection data is reset to 0 at 00:00 A.M.

Moreover, no correction can be performed at all at the predictive information corrector 122E.

When the image data generator 124 receives predictive data, the image data generator 124 generates data for displaying a predetermined image on the display based on predictive data. This generation of data is carried out based on Tables illustrated in FIG. 10 and FIG. 11 in this embodiment.

Namely, the image to be displayed is determined from predictive data, which is any one of A) safe, B) rather safe, C) slightly dangerous D) rather dangerous, and E) dangerous and a character level. The image includes a bear's moving image, and bear's lines.

The moving image includes a nap image in which the bear takes a nap, a resignation image in which the bear gives up and yawns, and the like. The bear's lines are as illustrated in FIG. 10 and FIG. 11. FIG. 10 is a Table, which is used when the user selects the beauty mode based on desirable data, and FIG. 11 is a Table, which is used when the user selects the bronze mode based on desirable data. An image, which is based on the user's desire, is displayed on the display 40 by the use of these Tables.

The character level is determined based on measurement data of the previous day. The character level is a numeral value whose initial value is 4. In the case where the cumulative ultraviolet ray quantity of the previous day is "D) rather dangerous", "−1" is put into the character level of the corresponding previous day. In the case where the cumulative ultraviolet ray quantity of the previous day is "E) dangerous", "−2" is put into the character level of the corresponding previous day. In the cases other than the above, "+1" is put thereinto.

Additionally, in the case where the cumulative ultraviolet ray quantity of the entire one day is less than 0.1 kJ/m2 and no input of button is performed all day, the character level is set to (±0), which is the same value as that of the previous day.

Image data for displaying the image as illustrated in the figure is generated based on the character level of the day and cumulative data at this point.

For example, in the case where the beauty mode is selected and the character level of the day is 5 and cumulative data (cumulative quantities) at this point is A), image data for displaying an image including a moving image indicating happy or normal and any one of liens "UV care is the primary key to beauty", "Hunh! Keep on going this way," and "Mmm, what a feeling!" is generated. In this embodiment, in the case where a plurality of alternatives of candidates in connection with the moving image and the lines is provided, any one of candidates can be selected at random.

In addition, the display of E) dangerous also has the meaning of the warning to the user. In the case where this display is continued a plurality of times, for example, four times and the user does not take any suitable measures (the user does not sit in the shade to reduce measurement data or the user does not input sun protection data), a reset is triggered.

When the reset is triggered, the image in which the bear waves its hand as saying good-by, and a series of measures performed so far is ended.

In this case, when the user depresses any one of input keys 20, measurement is started again. In this case, any one of comments, "the skin is more delicate than you think", "a hard suntan equals a burn", and "How is your skin condition? Is it fine?" is displayed on the display 40.

An explanation will be next given of processing for warning that the ultraviolet ray quantity is harmful to the user at this point. This processing is mainly carried out by the suntan condition predictor 122.

First, the reference setting section 123A sets a reference ultraviolet ray quantity, which is considered as being harmful to the user, based on characteristic data received. More specifically, the reference setting section 123A may set the reference ultraviolet ray quantity based on the reference Table as illustrated in FIG. 12. In this case, the range of 50~mW/cm$^2$ where the ultraviolet ray quantity is the largest is harmful to the user, and 50 mW/cm$^2$ is set as a reference ultraviolet ray quantity.

In this embodiment, a suitable change is added to characteristic data, whereby changing the reference ultraviolet ray quantity. For example, in the case where the characteristic of user's skin against suntan is level 3, which is the common level, this numeral value is used as it is. In the case where the skin is stronger than the common level, this reference may be increased by 5 mW/cm$^2$ every time when the skin level changes by one. In the case where the skin is more delicate than the common level, this reference may be decreased by 5 mW/cm$^2$ every time when the skin level changes by one.

Moreover, in the case where sun protection data about the SPF value of the sunscreen is not 0, this reference may be increased by 5 mW/cm$^2$.

Data about this reference ultraviolet ray quantity is sent to the main warning section 123B.

The main warning section 123B contrasts measurement data received from the main controller 121 with data about the reference ultraviolet ray quantity. Then, in the case where the ultraviolet ray quantity indicated by measurement data at this point exceeds the reference ultraviolet ray quantity, the main warning section 123B sends an instruction to the image data generator 124 to display the image of this fact. The image data generator 124 that has received such an instruction generates image data for displaying such a message of "UV warnings!" on the display.

In this embodiment, a sun mark whose number changes is always displayed on the display 40, whereby having the user grasped the ultraviolet ray quantity visually. In the case where the ultraviolet ray quantity is increased to the extent that is a little lower than the case in which the "UV warning!" is displayed, a message of "UV caution" urging the user to use caution is displayed. This image data is also generated by the image data generator 128. An instruction for this purpose is provided by e.g., the main warning section 128B.

In any case, the display 40 displays an image, which is based on image data received.

Additionally, a function for executing a predetermined game is provided to the aforementioned main controller, thereby making it possible to use this portable apparatus as a portable game apparatus.

Since the portable apparatus according to the present invention is as mentioned above, there can be provided an unconventional and novel portable apparatus that has an intermediate property between a measuring apparatus and a game apparatus.

Various embodiments and changes may be made thereunto without departing from the broad spirit and scope of the invention. The above-described embodiment intended to illustrate the present invention, not to limit the scope of the present invention. The scope of the present invention is shown by the attached claims rather than the embodiment. Various modifications made within the meaning of an equivalent of the claims of the invention and within the claims are to be regarded to be in the scope of the present invention.

What is claimed is:

1. A portable apparatus comprising:

measuring means for measuring a physical quantity which is associated with a factor affecting a user's skin condition to generate measurement data;

controlling means for predicting degree of change of a user's skin condition with time based on said measurement data to generate image data for displaying different images depending on the degree of change;

displaying means for displaying the images based on said image data; and a portable housing to which said measuring means, said controlling means, and said displaying means are attached, wherein said different images are grouped together into an image group, and a plurality of said image groups are provided, wherein at least one of the images in one said image group is different from the images in another said image group, and wherein one of the image groups is selected for displaying in accordance with a character level, wherein said character level is determined based on measurement data of the previous day.

2. The portable apparatus according to claim 1, wherein said controlling means comprises recording means for recording predictive data, which is data about influence exerted upon the user's skin by said factor and which is associated with said physical quantity of the factor, and extracting means for receiving said measurement data and for extracting the predictive data associated with said physical quantity about the factor indicated by said measurement data, and image data generating means for generating said image data based on said predictive data extracted by said extracting means.

3. The portable apparatus according to claim 1, further comprising first inputting means for receiving characteristic data about a characteristic of the user's skin in a manual input, said first inputting means being attached to said housing, and wherein said controlling means predicts the user's skin condition based on said measurement data and said characteristic data.

4. A portable apparatus comprising:

controlling means for receiving measurement data from predetermined measuring means for measuring a physical quantity about a factor affecting a user's skin condition to generate the measurement data, for predicting degree of change of a user's skin condition with time based on said received measurement data, and for generating image data for displaying different images depending on the degree of change;

displaying means for displaying the images based on said image data; and a portable housing to which said measuring means, said controlling means, and said displaying means are attached, wherein said different images are grouped together into an image group, and a plurality of said image groups are provided, wherein at least one of the images in one said image group is different from the images in another said image group, and wherein one of the image groups is selected for displaying in accordance with a character level, wherein said character level is determined based on measurement data of the previous day.

5. A method, which is executed by controlling means of a portable apparatus comprising controlling means for receiving measurement data from predetermined measuring means for measuring a physical quantity about a factor affecting a user's skin condition to generate the measurement data; displaying means for displaying predetermined image under control of said controlling means; a portable housing to which said controlling means and said displaying means are attached, said method executed by said controlling means comprising the steps of:

receiving said measurement data;

predicting degree of change of the user's skin condition with time based on said received measurement data; and generating image data for displaying different images, which are depending on the degree of change, on said display means, wherein said different images are grouped together into an image group, and a plurality of said image groups are provided, wherein at least one of the images in one said image group is different from the images in another said image group, and wherein one of the image groups is selected for displaying in accordance with a character level, wherein said character level is determined based on measurement data of the previous day.

6. A portable apparatus comprising:

an ultraviolet sensor for measuring an ultraviolet ray quantity to generate measurement data about the ultraviolet ray quantity;

first inputting means for receiving characteristic data about a characteristic of a user's skin against a suntan in a manual input;

controlling means for predicting degree of change of a user's suntanned skin condition with time based on said measurement data and said characteristic data to generate image data for displaying different images about the prediction of the user's suntanned skin condition depending on the degree of change;

displaying means for displaying the images about the prediction of the user's suntanned skin condition based on said image data; and a portable housing to which said ultraviolet sensor, said controlling means, and said displaying means are attached, wherein said different images are grouped together into an image group, and a plurality of said image groups are provided, wherein at least one of the images in one said image group is different from the images in another said image group, and wherein one of the image groups is selected for displaying in accordance with a character level, wherein said character level is determined based on measurement data of the previous day.

7. The portable apparatus according to claim 6, wherein said controlling means comprises:

recording means for recording predictive data, which is data about a degree of the suntan occurred on the user's skin with ultraviolet rays and which is associated with the ultraviolet ray quantity and the characteristic of the user's skin;

extracting means for receiving said measurement data and said characteristic data and for extracting the predictive data associated with the ultraviolet ray quantity indicated by said measurement data and the characteristic of the skin indicated by said characteristic data; and image data generating means for generating said image data based on said predictive data extracted by said extracting means.

8. The portable apparatus according to claim 6, wherein said controlling means calculates cumulative data about a cumulative ultraviolet ray quantity, which is a cumulative value of the ultraviolet ray quantities after the start of measurement based on measurement data sequentially received after the start of measurement, and predicts the user's suntanned skin condition based on said cumulative data and said characteristic data.

9. The portable apparatus according to claim 8, wherein said controlling means comprises:

recording means for recording predictive data, which is data about a degree of the suntan occurred on the user's skin with ultraviolet rays and which is associated with the ultraviolet ray quantity and the characteristic of the user's skin;

extracting means for receiving said cumulative data and said characteristic data and for extracting the predictive data associated with the ultraviolet ray quantity indicated by said cumulative data and the characteristic of the skin indicated by said characteristic data; and image data generating means for generating said image data based on said predictive data extracted by said extracting means.

10. The portable apparatus according to claim 8, further comprising second inputting means for receiving desirable data about a user's suntan desire as to which the user desires promotion of a suntan or protection of suntan, and wherein said controlling means predicts a user's suntanned skin condition based on said cumulative data and said characteristic data, reflects the user's suntan desire based on the prediction and said desirable data, and generates image data for displaying images, which are depending on the prediction of the user's suntanned skin condition, on said display device.

11. The portable apparatus according to claim 8, further comprising second inputting means for receiving desirable data about a user's suntan desire as to which the user desires promotion of a suntan or protection of suntan, third inputting means for receiving sun protection data relating to means for protecting the suntan used by the user, and wherein said controlling means predicts the user's suntanned skin condition based on said cumulative data, said characteristic data, and said sun protection data, and generates said image data based on the prediction and said desirable data.

12. The portable apparatus according to claim 6, further comprising second inputting means for receiving desirable data about a user's suntan desire as to which the user desires promotion of a suntan or protection of suntan, and wherein said controlling means predicts a user's suntanned skin condition based on said measurement data and said characteristic data, reflects the user's suntan desire based on the prediction and said characteristic data, and generates image data for displaying images, which are depending on the prediction of the user's suntanned skin condition, on said display device.

13. The portable apparatus according to claim 6, further comprising
second inputting means for receiving desirable data about a user's suntan desire as to which the user desires promotion of a suntan or protection of suntan,
third inputting means for receiving sun protection data relating to means for protecting the suntan used by the user, and
wherein said controlling means predicts the user's suntanned skin condition based on said measurement data, said characteristic data, and said sun protection data, and generates said image data based on the prediction and said desirable data.

14. A portable apparatus according to claim 6 further comprising:
reference setting means for setting a reference ultraviolet ray quantity, which is the ultraviolet ray quantity judged as being dangerous to a user; and
warning means for receiving said measurement data, for determining whether or not said ultraviolet ray quantity indicated by said measurement data exceeds said reference ultraviolet ray quantity, and when said ultraviolet ray quantity indicated by said measurement data exceeds said reference ultraviolet ray quantity, for generating image data for displaying an image indicating the excess of said ultraviolet ray quantity;
wherein said displaying means further displaying an image indicating a warning that a current ultraviolet ray quantity is harmful to the user based on said image data generated by said warning means; and
wherein said reference setting means and said warning means are attached to said portable housing.

15. A portable apparatus according to claim 6 further comprising:
reference setting means for receiving said characteristic data and for setting a reference ultraviolet ray quantity, which is the ultraviolet ray quantity judged as being dangerous to a user; and
warning means for receiving said measurement data, for determining whether or not said ultraviolet ray quantity indicated by said measurement data exceeds said reference ultraviolet ray quantity, and when said ultraviolet ray quantity indicated by said measurement data exceeds said reference ultraviolet ray quantity, for generating image data for displaying an image indicating the excess of said ultraviolet ray quantity;
wherein said displaying means further displaying an image indicating a warning that a current ultraviolet ray quantity is harmful to the user based on said image data generated by said warning means; and
wherein said reference setting means and said warning means are attached to said portable housing.

16. The portable apparatus according to claim 15, further comprising
third inputting means for receiving sun protection data relating to means for protecting the suntan used by the user, and
wherein said reference setting means sets said reference ultraviolet ray quantity based on said characteristic data and said sun protection data.

17. A portable apparatus comprising:
first inputting means for receiving characteristic data about a characteristic of a user's skin against a suntan in a manual input;
controlling means for receiving said characteristic data from said first inputting means and measurement data from a predetermined ultraviolet sensor that measures an ultraviolet ray quantity to generate said measurement data about the ultraviolet ray quantity, and predicts degree of change of a user's suntanned skin condition with time based on said received measurement data and said characteristic data to generate image data for displaying different images about the prediction of the user's suntanned skin condition depending on the degree of change;
displaying means for displaying the images about the prediction of the user's suntanned skin condition based on said image data; and
a portable housing to which said ultraviolet sensor, said controlling means, and said displaying means are attached,
wherein said different images are grouped together into an image group, and a plurality of said image groups are provided, wherein at least one of the images in one said image group is different from the images in another said image group, and
wherein one of the image groups is selected for displaying in accordance with a character level, wherein said character level is determined based on measurement data of the previous day.

18. A portable apparatus according to claim 17 further comprising:
reference setting means for receiving said characteristic data and for setting a reference ultraviolet ray quantity, which is the ultraviolet ray quantity judged as being dangerous to a user; and
warning means for receiving measurement data from a predetermined ultraviolet sensor for measuring said ultraviolet ray quantity to generate said measurement data about the ultraviolet ray quantity, for determining whether or not said ultraviolet ray quantity indicated by said measurement data exceeds said reference ultraviolet ray quantity, and when said ultraviolet ray quantity indicated by said measurement data exceeds said reference ultraviolet ray quantity, for generating image data for displaying an image indicating the excess of said ultraviolet ray quantity;
wherein said displaying means further displaying an image indicating a warning that a current ultraviolet ray quantity is harmful to the user based on said image data generated by said warning means; and
wherein said reference setting means and said warning means are attached to said portable housing.

19. A method, which is executed by controlling means of a portable apparatus comprising controlling means for receiving measurement data from a predetermined ultraviolet sensor for measuring an ultraviolet ray quantity to generate measurement data about the ultraviolet ray quantity; displaying means for displaying a predetermined image under control of said controlling means; a portable housing to which said controlling means and said displaying means are attached, said method executed by said controlling means comprising the steps of:
receiving said measurement data;
predicting degree of change of the user's skin condition with time based on said received measurement data; and generating image data for displaying different images, which are depending on the degree of change, on said display means, wherein said different images are grouped together into an image group, and a plurality of said image groups are provided, wherein at least one of the images in one said image group is different from the images in another said image group, and wherein one of the image groups is selected for displaying in accordance with a character level, wherein said character level is determined based on measurement data of the previous day.

20. A method according to claim 19, wherein said portable apparatus further comprising:

first inputting means for receiving characteristic data about a characteristic of a user's skin against a suntan in a manual input; and reference setting means for receiving said characteristic data and for setting a reference ultraviolet ray quantity, which is the ultraviolet ray quantity judged as being dangerous to a user;

wherein said controlling means further receiving said measurement data and said characteristic data to generate predetermined image data based on these data; and wherein said first inputting means and said reference setting means are attached to said portable housing;

said method executed by said controlling means comprising the steps of:

receiving said characteristic data to set a reference ultraviolet ray quantity, which is the ultraviolet ray quantity judged as being dangerous to a user;

receiving said measurement data to determine whether or not said ultraviolet ray quantity indicated by said measurement data exceeds said reference ultraviolet ray quantity; and generating image data, when said ultraviolet ray quantity indicated by said measurement data exceeds said reference ultraviolet ray quantity, for displaying an image indicating the excess of said ultraviolet ray quantity.

* * * * *